(12) United States Patent
Haystead et al.

(10) Patent No.: US 6,716,395 B2
(45) Date of Patent: Apr. 6, 2004

(54) INTEGRATED PROTEIN AFFINITY CAPTURE CENTRIFUGATION DEVICE

(75) Inventors: Timothy A. J. Haystead, Chapel Hill, NC (US); George J. Young, Harvard, MA (US)

(73) Assignee: Serenex, Inc., Durham, NC (US)

( * ) Notice: Subject to any disclaimer, the term of this patent is extended or adjusted under 35 U.S.C. 154(b) by 26 days.

(21) Appl. No.: 10/022,931

(22) Filed: Dec. 18, 2001

(65) Prior Publication Data

US 2003/0113938 A1 Jun. 19, 2003

(51) Int. Cl.[7] .......................... G01N 9/30; G01N 35/00
(52) U.S. Cl. ............................ 422/72; 422/99; 435/7.1; 435/287.1; 435/DIG. 15; 435/DIG. 43; 435/DIG. 45; 436/518; 436/43; 436/45; 436/173; 436/177; 436/178
(58) Field of Search .................. 422/68.1, 72, 99, 422/100, 101; 435/7.1, 6, 4, 287.1, DIG. 1, DIG. 2, DIG. 14, DIG. 15, DIG. 43, DIG. 45; 436/518, 43, 45, 173, 177, 178

(56) References Cited

U.S. PATENT DOCUMENTS

| | | | |
|---|---|---|---|
| 5,536,822 A | 7/1996 | Haystead | 536/26.26 |
| 6,214,617 B1 | 4/2001 | Herman | |
| 6,274,088 B1 * | 8/2001 | Burbaum et al. | 422/101 |
| 6,309,875 B1 | 10/2001 | Gordon | |
| 2002/0001803 A1 | 1/2002 | Smith | |
| 2002/0055110 A1 | 5/2002 | Tomlinson et al. | |
| 2002/0058273 A1 | 5/2002 | Shipwash | |

FOREIGN PATENT DOCUMENTS

| | | |
|---|---|---|
| WO | WO 94/05394 | 3/1994 |
| WO | 00/55625 * | 9/2000 |
| WO | WO 00/63694 | 10/2000 |

OTHER PUBLICATIONS

Haystead, T.A.J. and G.J. Young "Proteome mining: exploiting serendipity in drug discovery," *Current Drug Discovery* [online], pp. 22–24 (Mar. 2001,). Retrieved from: www.currentdrugdiscovery.com.

Damer, C.K., et al., "Rapid Identification of Protein Phosphatase 1–binding Proteins by Mixed Peptide Sequencing and Data Base Searching," *The Journal of Biological Chemistry*, 273(38) : 24396–24405, (1998).

Davies, S.P., et al., "Purification of the AMP–activated protein kinase on ATP–gamma–sepharose and analysis of its subunit structure," *Eur. J. Biochem*, 223(2) : 351–357, (1994).

Handfield, M., and Levesque R.C., "Strategies for isolation of in vivo expressed genes from bacteria," *FEMS Microbiol Rev.*, 23(1) : 69–91, (1999).

* cited by examiner

*Primary Examiner*—Maureen M. Wallenhorst
(74) *Attorney, Agent, or Firm*—Alston & Bird LLP

(57) ABSTRACT

A method and apparatus are described for screening a proteome. The method and apparatus include an array of affinity elements, such that a proteome is directed through the array and those components that specifically bind to the affinity elements of the array are eluted in a suitable eluent by means of centrifugation. Suitable eluents can include a proteome component, a chemical library component or an affinity element. This method and apparatus can be used for several purposes, including screening for bio-active compounds, determining physiological targets of known drugs, determining specificity of compound interactions with physiological targets, and for quantitative protein analyses.

18 Claims, 8 Drawing Sheets

US 6,716,395 B2

INTEGRATED PROTEIN AFFINITY CAPTURE CENTRIFUGATION DEVICE

BACKGROUND OF THE INVENTION

Proteomics is an emerging technology for the study of protein function that has arisen in the post-genomics era. As the entire genomes of different organisms of the animal, plant, prokaryotic and viral kingdoms are being sequenced, thousands of genes are being identified, and these genes encode an abundance of distinct proteins. These proteins, the proteome of an organism, are being studied for identification of new drugs or commercially-important bio-active molecules.

Now the search for better therapeutics is being driven by several factors which need to be discovered: the identity and role of protein targets whose function may be pivotal for disease progression; the molecules that interact with these protein targets to attenuate their function and cause a therapeutic effect; the key biochemical pathways and the manner in which proteins interact with each other, which is critical for the selection of the most appropriate target for therapeutic intervention; and the impact of therapeutic candidates on the whole organism, including the most common variants of important proteins to identify potential side-effects and toxicity (the pharmacogenomic profile) of drug candidates as rapidly as possible.

The traditional approaches to drug discovery are either by selective drug design methods, which to date are at best, an inexact science, or by screening test compounds in a disease model. Screening, historically, has been the most effective of the two methods for identifying therapeutics, but it is labor-intensive. Most screening has been of randomly-selected candidates. More recently, screening has included the use of combinatorial libraries of candidate drugs, or portion thereof. Generally however, the techniques used to screen libraries, such as liquid chromatography, have been slow and expensive.

Therefore, a need exists for an apparatus and method to screen candidate therapeutic drugs that significantly reduce of eliminate the above-mentioned problems.

SUMMARY OF THE INVENTION

The present invention is generally directed to a method for screening a proteome, which is a mixture of proteins or compounds derived from a common source, and an apparatus for screening a proteome.

In one embodiment, the method for screening a proteome includes passing the proteome though an array of elements that possess an affinity for at least one compound in the proteome. This is followed by washing the array to remove those compounds of the proteome that do not specifically bind, and subsequently directing an eluent through the array by centrifugal force, which releases the specifically-bound compound, and elutes the released compound, thereby screening the proteome.

In another embodiment, an apparatus is provided to screen a proteome. The apparatus includes an array of affinity elements that includes at least one ligand, and means to apply a centrifugal force to the array such that, in the presence of an eluent, the compound of the proteome that is bound to the ligand can be eluted from the affinity element by centrifugation.

This invention has many advantages. For example, proteomes can be screened rapidly and systematically, whereby not only new lead compounds can be identified, but also the identity of the physiological targets of known drugs. Use of an affinity array enables efficient and quantitative capture of proteins, even when proteins are present in small quantities. This is important since disease-causing proteins, such as transcription factors or kinases, are often present in low copy numbers in a cell. Furthermore, the amount of protein captured can be directly measured. The use of small bed volumes of resin enables the enrichment of targeted proteins and proteomes. By employing centrifugal force to direct an eluent through the affinity array, the total volume of the eluent applied to the array can be recovered, which contrasts with flow-type elution methods that generally result in larger elution volumes and therefore greater dilution of the eluate. Thus, relatively small volumes of eluents can be applied to the affinity array, which can result in significantly more efficient recovery of proteins that are readily amenable to subsequent manipulation. For example, because the eluted proteins are concentrated in a small volume, they typically can be directly sampled for MALDI-TOF mass spectrometry or ICAT analysis without further manipulation. This generally provides for more rapid identification of targets. Furthermore, potential toxicity can be assessed by sequencing proteins that are simultaneously eluted. Unlike many known methods of designing improved therapeutic compounds, this invention can also be used to identify physiological targets of known drugs, the mechanism of action of which was previously unknown. By identifying the physiological target of the known drug using this invention, the mechanism of action can be assessed and improved targets can be identified. Furthermore, this invention can be automated and integrated into a robotics system.

DETAILED DESCRIPTION OF THE INVENTION

The features and other details of this invention, either as steps of the invention or as combinations of parts of the intention, will now be more particularly described and pointed out in the claims. It will be understood that the particular embodiments of the invention are shown by way of illustration and not as limitations of the invention. The principle features of this invention can be employed in various embodiments without departing form the scope of the invention.

Affinity element as defined herein, refers to a component that is a candidate for interacting with, or being a ligand for, at least one element in a proteome or combinatorial library. Such affinity elements include, but are not limited to, purines and purine analogs such as ATP, AMP, ADP, NADH. Also included are chemical, peptide or oligonucleotide libraries, which may be separately screened with a proteome or portion thereof.

The present invention is generally directed to a method and apparatus for screening a proteome for bio-active compounds of interest. Typical methods already known in the art for screening a proteome are described in WO 00/636694, filed Apr. 12, 2000, the teachings of which are incorporated herein by reference in its entirety.

Figure 1:
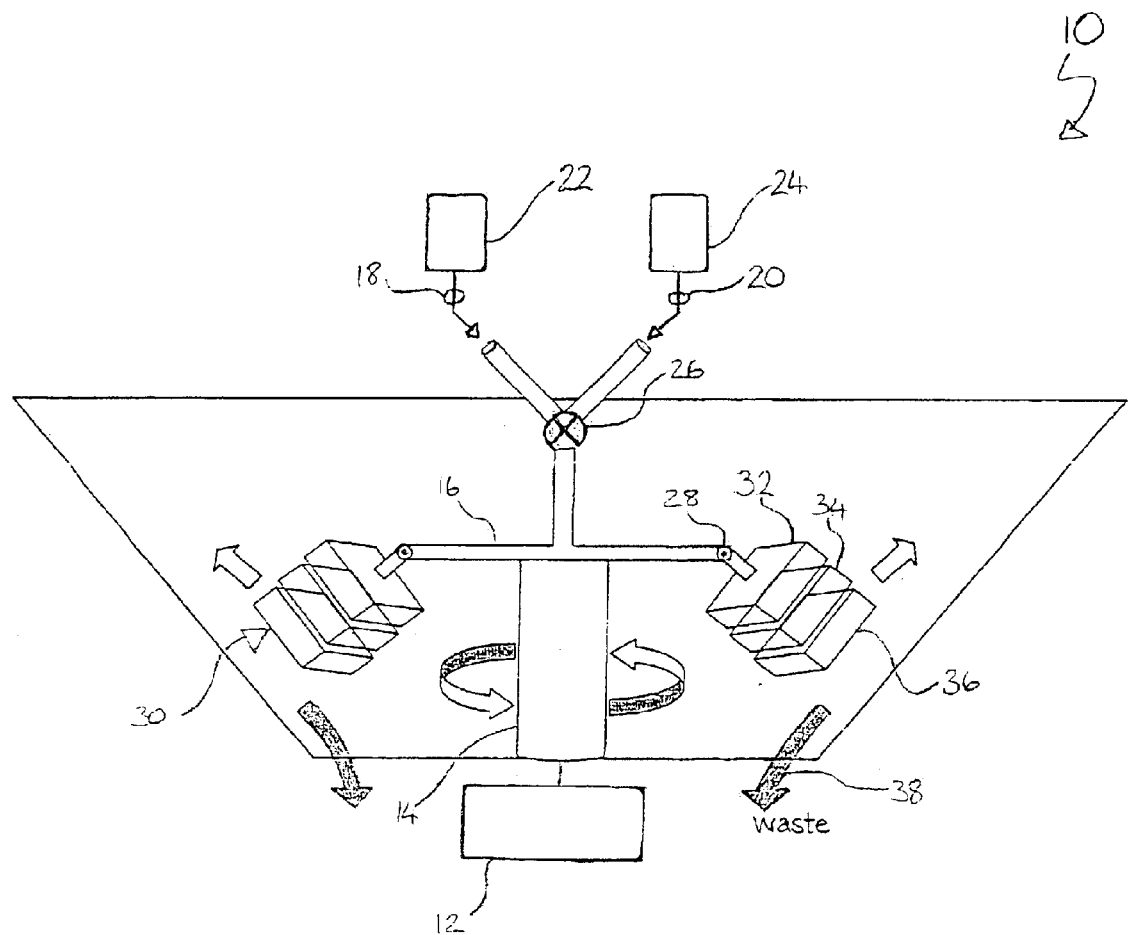
FIG. 1 is a schematic representation of a stacked column centrifugal liquid chromatography apparatus suitable for conducting the method of the invention.

Referring to FIG. 1, shown therein is apparatus 10, which is one embodiment of apparatus that is suitable for practicing the method of the invention. The apparatus includes a centrifuge, which can be temperature-regulated, with rotor 12, attached to spindle 14, to which rotor arms 16 are attached. To rotor arms 16, one or more fluid conduits 18 and 20 are connected, which supplies fluid from fluid sources 22 and 24, respectively. The fluids from fluid sources 22 and 24 can be regulated by valve 26. Attached to the end of rotor arms 16 is hinge 28, to which stacked trays 30 are attached. The application of a centrifugal force about the axis of rotation will cause stacked trays 30 to rotate about hinge 28 and thereby cause stacked trays 30 to become parallel with the centrifugal force. In one embodiment, stacked trays 30 include sample tray 32, also referred to herein as a tube sheet, that contain sample, for example and without limitation, a proteome sample or fraction thereof, or a combinatorial library sample or fraction thereof. In a further embodiment, the stacked trays include at least one tray that contains affinity array 34 to be screened, and at least one tray 36 that can collect eluate.

To perform the screening of affinity array 34, a centrifugal force is applied to stacked trays 30. Compounds specifically bound to affinity array 34 are eluted from affinity array 34 by means of directing at least one eluent through affinity array 34 by centrifugation, wherein the eluent releases the bound compounds from affinity array 34 as a component of the eluate, thereby screening the proteome. In one embodiment, sample in array 32 depicted in FIG. 1, flows through affinity array 34. Compounds of the sample in array 32 that specifically bind to an affinity element of affinity array 34 are retained in affinity array 34, whereas compounds that do not bind to the affinity element elute into collection array 36. Additionally or alternatively, the means of applying an eluent to an array can be through one or more conduits 18 or 20 that can be further regulated at valve 26. In a further embodiment, at least affinity array 34 can be washed before and/or after applying the sample, by applying a wash solution to affinity array 34 using centrifugation, thereby removing non-specifically binding components from affinity array 34. In one embodiment, the wash solution is a low ionic buffer. In another embodiment, the wash solution is a high ionic buffer. The specifically-bound compounds are eluted from affinity array 34 by means of directing at least one eluent through affinity array 34 by centrifugation, wherein the eluent releases the bound compounds from the affinity element as a component of the eluate. Waste materials can be removed from the centrifuge unit by means of waste conduit 38.

In one embodiment, stacked trays 30 are contained within a swing basket or bucket that can support stacked trays 30.

Figure 2:
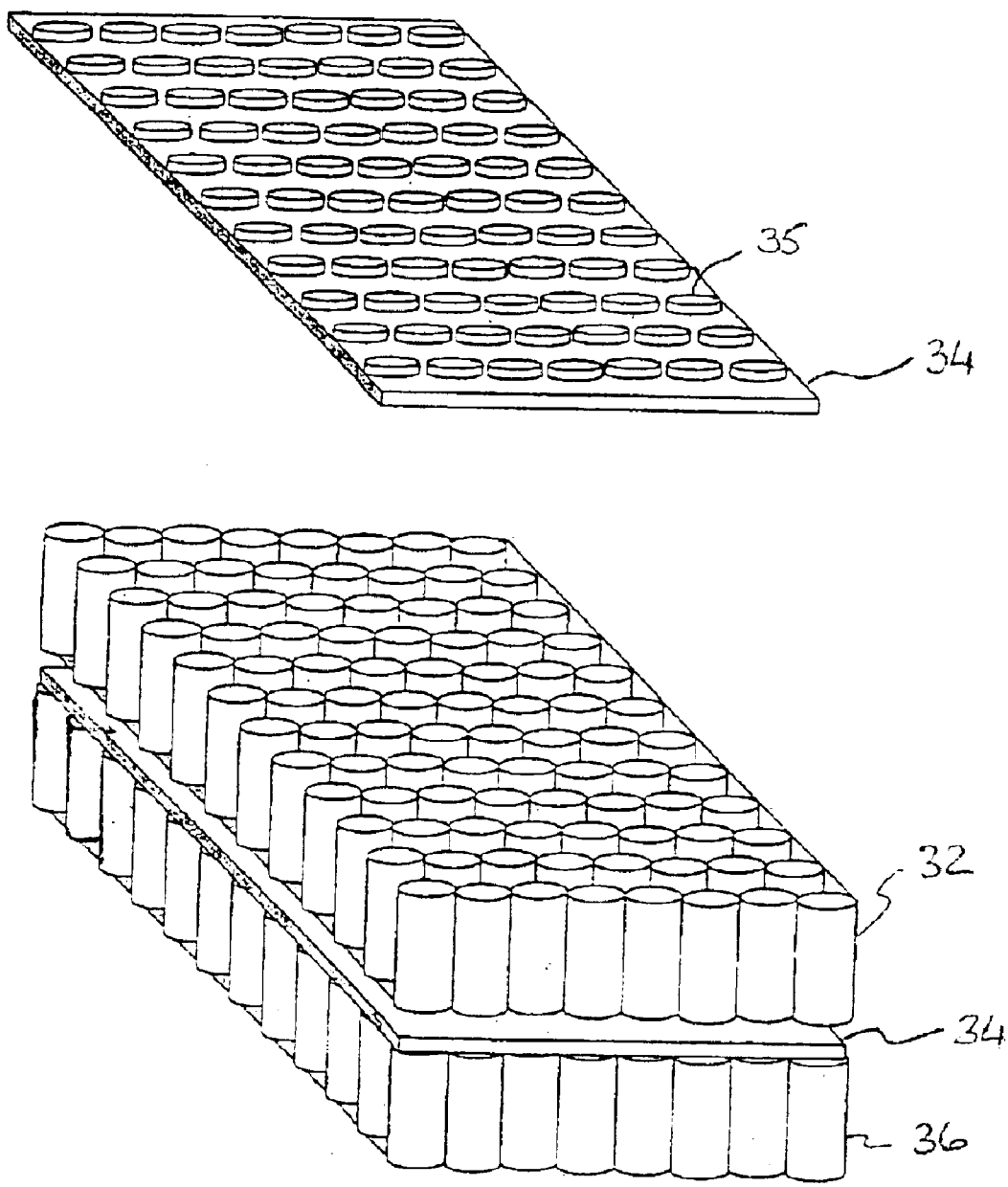
FIG. 2 depicts a sheet of affinity column discs and the stacking of tubes of sample on top of a sheet of affinity column discs on top of collection tubes in 96 well-type format.

As represented in FIG. 2, affinity array 34 includes suitable affinity elements 35. Examples of suitable affinity elements 35 are columns or discs. In one embodiment, affinity array 34 includes at least twelve affinity elements. In another embodiment, affinity array 34 includes at least ninety-six affinity elements. Affinity array 34 can be located between arrays 32 and 36 so that one or more affinity elements can be aligned with the affinity elements of affinity array 34, or the affinity elements can be intentionally misaligned. In one embodiment, affinity array 34 has at least one element that is at least one physiological target candidate or ligand of a protein component of the proteome to be screened. In a preferred embodiment, the physiological target is adenosine triphosphate (ATP) or a structural analog thereof. In a specific embodiment, the ATP is bound to an inert support in a uniform orientation. Inert supports suitable for use in the invention will be recognized by those of skill in the art. Without limitation, examples of suitable resins for use as an inert support include bead or monolithic resins, such as those used for chromatography, and which are composed of a base matrix such as polyacrylamide, agarose, coated silica-beads, cellulose, polystyrene divinylbenzene, methacrylate or polymethacrylate, and the like. Typically, a suitable polyacrylamide inert support can be selected from CM Hyper D® (F grade) and ceramic Hyper D®; a suitable agarose inert support can be Sepharose® Fast Flow; a suitable silica inert support can be BAKERBOND PEI™; a suitable polystyrene divinylbenzene inert support can be Amberchrom®; a suitable methacrylate or polymethacrylate inert support can be selected from Macro-Prep® DEAE, and Macro-Prep® high S, a suitable hydrophilic polymer matrix inert support can be Toyopearl® Butyl-650M; and a suitable composite or monlithic inert support can be selected from UNO™ Sphere Q and UNO™ Sphere S. Preferably, the ATP is bound to the inert support at the gamma phosphate portion of the ATP, thus exposing the adenosine portion of the ATP to solutions or eluents directed through the array. Typical methods already known in the art for linking an ATP moiety to an inert support are described in U.S. Pat. No. 5,536,822, filed Mar. 9, 1994, the teachings of which are incorporated herein by reference in their entirety. In another preferred embodiment, the eluent comprises at least one purine or purine analog. In one embodiment, the purine analog is naturally-occurring. In a specific embodiment, the purine analog is selected from the group consisting of NADH, AMP, ADP and ATP.

In another embodiment, the physiological target is bound to an inert support in an orientation different from an identical physiological target bound to another inert support in another orientation.

Another embodiment of the invention provides for each element in affinity array 34 to have a plurality of physiological targets or ligands. In a particularly preferred embodiment, the number of physiological targets or ligands in each element in affinity array 34 is at least about ten. A further embodiment of this invention provides for the whole proteome of interest to be distributed among the elements of affinity array 34.

In a further embodiment of the invention, the concentration of the physiological target on at least a portion of the elements of affinity array 34 is at least about 50 μmoles to at least about 100 μmoles per milliliter of element. More preferably the concentration of the physiological target on at least a portion of the elements of affinity array 34 is at least about 10 μmoles per milliliter of the element.

Furthermore, in another preferred embodiment, the amount of proteome that is directed through affinity array 34 is sufficient to recover at least about 0.1 pmol to at least about 1 pmol of a component of the proteome that binds to the physiological target on affinity array 34.

Generally, the eluent includes a component from a chemical library in a concentration ranging from about 1 nM to about 500 mM, more preferably ranging from about 10 nM to about 1 mM. The chemical library component of the eluent includes at least a single molecule. In a preferred embodiment, the chemical library component includes at least ten structurally non-related molecules. The component of the chemical library is preferably soluble in a physiologically-compatible solution. In a preferred embodiment the physiologically-compatible solution is an aqueous solution. In an alternative embodiment, the solution contains an organic solvent. An example of an organic solvent solution is dimethyl sulphoxide (DMSO), preferably in a concentration range of up to about 10% (volume/volume).

In an additional embodiment, the elements of affinity array 34 and the eluent each include a portion of at least one chemical library.

In another embodiment of the invention, at least a portion of the elements of affinity array 34 includes an amount of resin packing in a range of between about 50 μl and about 100 μl.

Preferably, the volume of eluent directed through each affinity element 35 of array 34 is in a range of between about 10 μl and about 100 μl. In one embodiment, the eluent includes a single component which is a candidate for selective release of a proteome component from affinity element 35. In a further embodiment, the eluent includes a plurality of distinct components that are candidates for the ability to selectively release and elute a proteome component from affinity element 35. Additionally, one embodiment of the invention provides for the eluent to include at least about ten distinct components that are candidates for release of a proteome component from affinity element 35. In another embodiment, the eluent includes at least a portion of a chemical library.

In one embodiment, affinity array 34 is screened by competitive binding with an eluent containing a proteome component. In another embodiment, affinity array 34 is screened by competitive binding with an eluent containing an affinity element. In an alternative embodiment, affinity array 34 is screened by competitive binding with an eluent containing a chemical library component.

It is believed that use of these arrays provide flexibility in the types of combinations of proteins, substrates and targets in a combinatorial library that can be effectively screened. Together with the control over experimental conditions possible with centrifugation, a wide variety of targets can be screened in a small fraction of the time generally necessary using known techniques.

Figure 3:
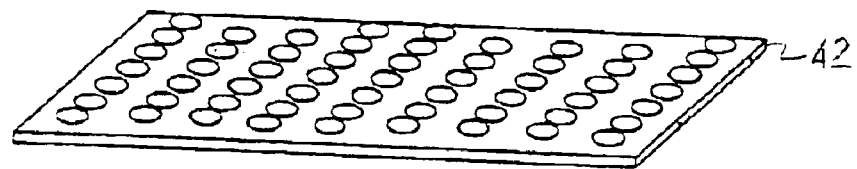
FIG. 3 depicts collection trays which can be controlled in an open or closed position according to the position of the valves.
Figure 3:
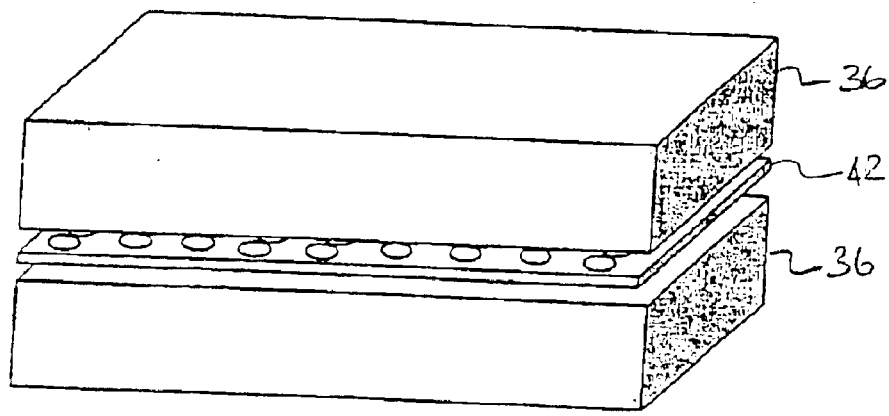
Figure 3:
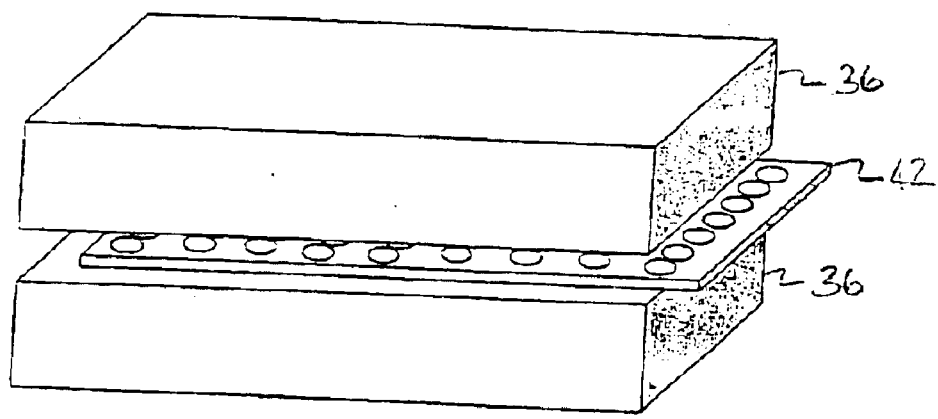

In one embodiment of the apparatus of the invention, as depicted in FIG. 3, stacked trays of tube sheets or collection trays 36 can be separated by means of slider valves 42, which can be positioned such that the open position of the valve is aligned with the orifices of two adjacent tube sheets or collection trays 36, whereby fluid communication between the tube sheets or collection trays 36 is achieved. Lateral movement of slider valve 42 positions valve 42 such that fluid communication between the adjacent tube sheets or collection tubes 36 is interrupted. Change in the position of slider valve 42 can be achieved by such means as magnetic force that may be remotely activated.

Figure 4:
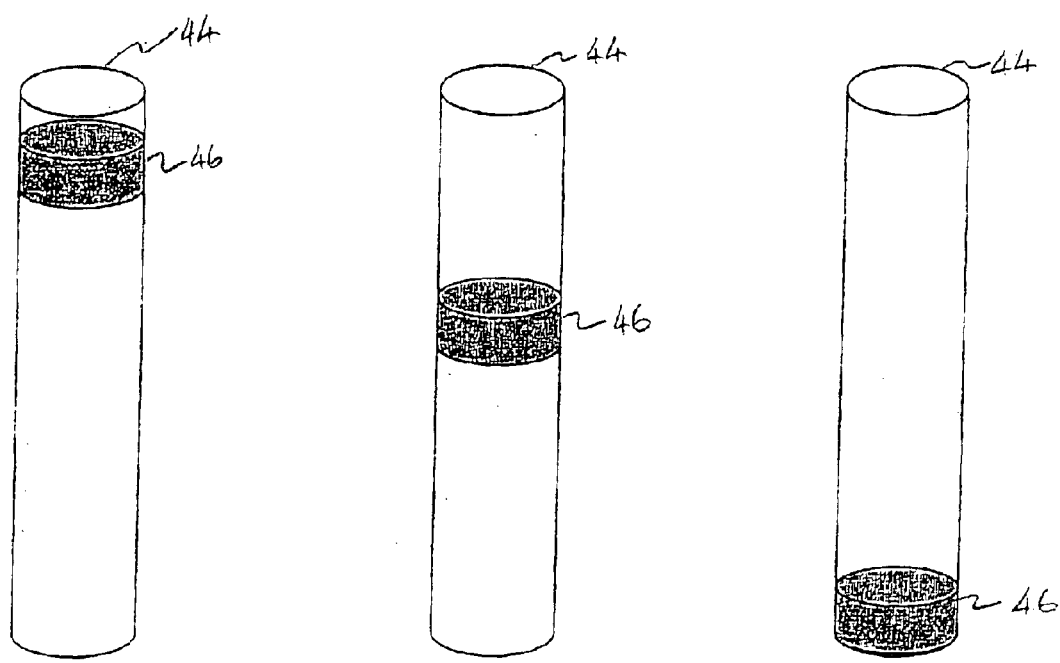
FIG. 4 represents a single column with a sliding tell disc.

In a further embodiment, depicted in FIG. 4, "tell discs" 46 are provided. Tell disc 46 is buoyant and provides a means to indicate the fluid level within tube 44. In another embodiment, tell disc 46 is capable of sealing the bottom of tube 44 in the absence of fluid.

Figure 5:
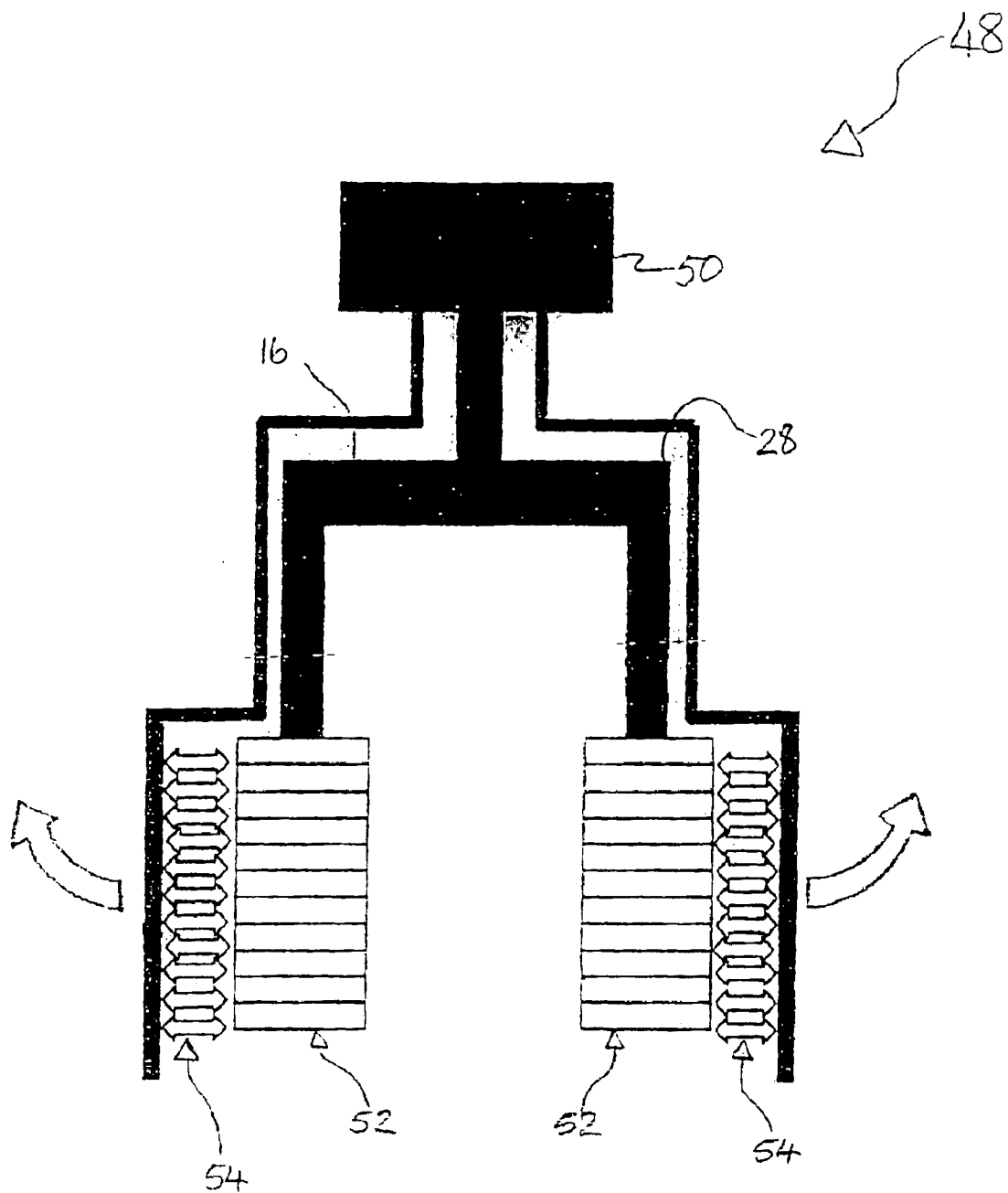
FIG. 5 is a schematic representation of a stacked column centrifugal liquid chromatography apparatus suitable for conducting the method of the invention which can be remotely controlled.
Figure 6:
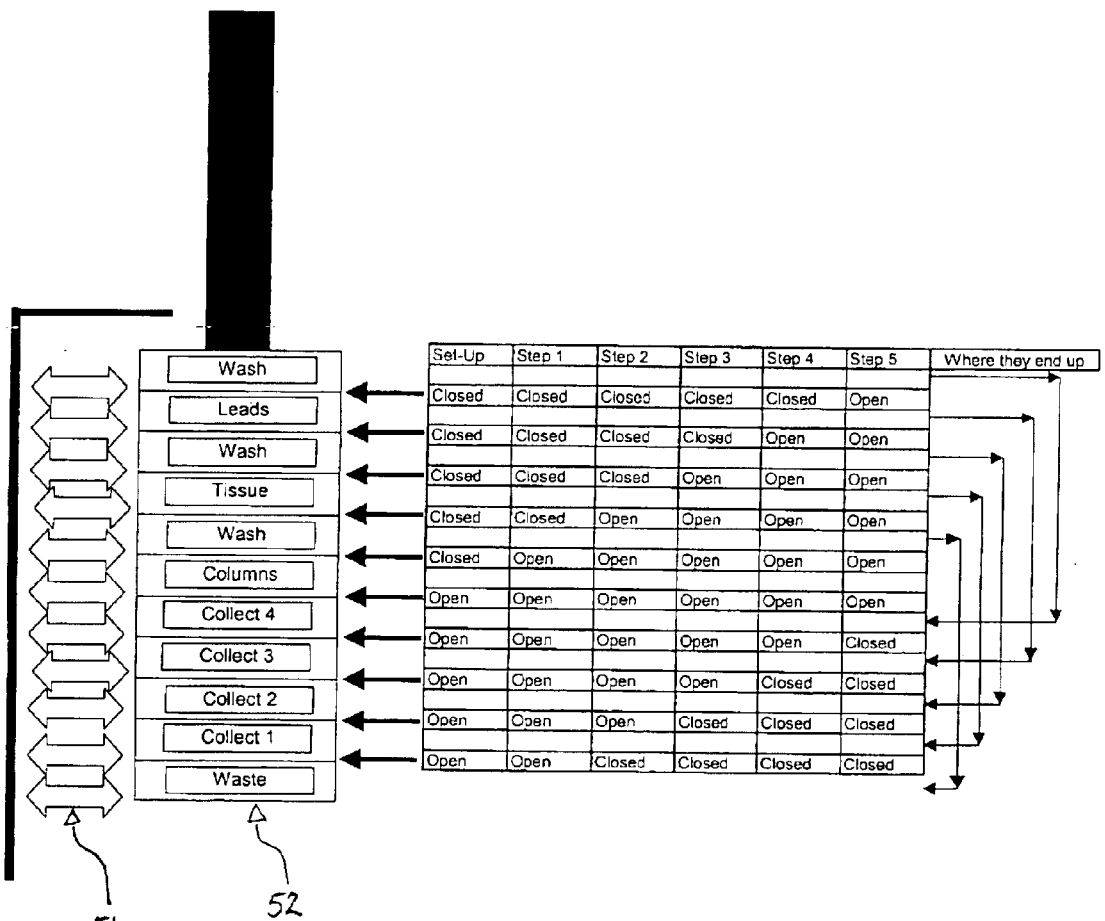
FIG. 6 details a general method to sequentially apply eluents and collect eluates through a stacked column centrifugal liquid chromatography apparatus.

FIG. 5 depicts a further embodiment of the invention, apparatus 48. Attached to electronic receiver 50, which can be magnetically activated and remotely controlled, are rotor arms 16 connected via hinge 28 to a series of stacked trays 52. The application of a centrifugal force will raise stacked trays 52 to be parallel with the centrifugal force. In a series of steps, magnetic couplers 54 can be sequentially activated and deactivated to manipulate valves within stacked trays 52, thereby selectively directing flow of proteome washes and eluents through affinity arrays 34 of stack trays 52. In a detailed schematic shown in FIG. 6, selective direction of flow through the individual trays in stack 52 is depicted. The flow of each solution through an array is indicated as magnetic coupler 54 activates and deactivates the opening and closing of the connecting orifices between trays of stack 52.

The eluate obtained using the method and apparatus of the invention is subsequently characterized by SDS-PAGE, MALDI-TOF mass spectrometry, liquid chromatography electrospray ionization tandem mass spectrometry (LC ESI MS/MS) or ICAT mass spectrometry, or by other suitable methods as will be appreciated by one of skill in the art, to identify fractions that contain either single proteins, or a mixture of a small number of proteins. These fractions are further analyzed by microsequencing. Mixed peptide sequencing may be performed as described in Damer et al., (1998) J. Biol. Chem. 273: 24396–24405; Alms et al., (1999) EMBO J. 18: 4157–4168, the teachings of which are incorporated herein by reference in their entirety. The mixed sequence data is subsequently processed using the algorithms, for example, FASTF or TFASTF, to sort and match the data with protein and DNA databases, respectively. Alternatively, other algorithms can be utilized to analyze the sequence data as will be appreciated by those who are skilled in the art. The biological significance of the identified protein is then assessed.

Figure 7:
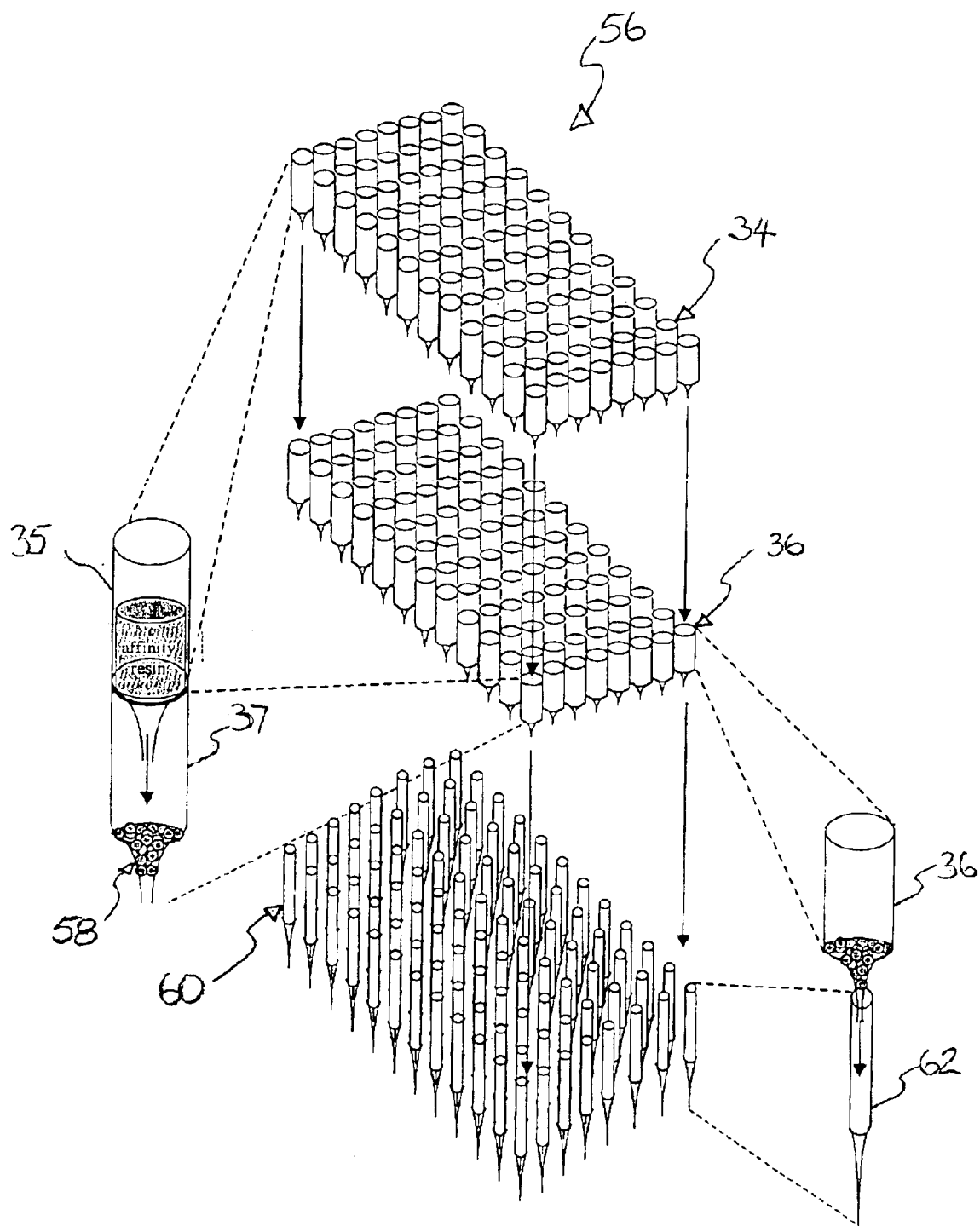
FIG. 7 is a schematic representation of an apparatus suitable for conducting the method of the invention that uses an array of nano-needles to collect eluates for analysis.

One embodiment of an apparatus for identifying eluate proteins is depicted in FIG. 7. As shown in FIG. 7, apparatus 56 includes affinity array 34 which interfaces with collection tray 36, also referred to herein as capture array 36, such that elution of eluates by centrifugation captures the eluates in collection tray 36. In a preferred embodiment, column 37 of collection tray 36 contains hydrophobic resin 58. Hydrophobic resins suitable for use in the invention will be recognized by those of skill in the art. Without limitation, an example of a suitable hydrophobic resin include POROS® R2. In one embodiment, the amount of hydrophobic resin 58 is between about 2 μl and about 4 μl. Subsequently, collection array 36 is disengaged from affinity array 34 and the eluate contained in collection array 36 is washed using buffers suitable for removal of unbound components and/or drug molecule(s), as will be appreciated by one of skill in the art. Collection array 36 is then washed with buffer, such as a protease buffer, and incubated with, for example, buffer containing a digestive enzyme, such as trypsin. Fluid flow through collection array 36 is stopped, preferably for a period of time in a range of between about 6 hours and about 8 hours, before collection array 36 is interfaced with nano-needle array 60 and centrifuged to collect digested eluate in nano-needle array 60. Other methods to digest or otherwise fractionate the eluate into a preparation suitable for analysis, for example, by mass spectrometry, will be appreciated by one of ordinary skill in the art. Digested eluate from column 37 of collection array 36 elutes into a corresponding nano-needle 62 of nano-needle array 60.

Figure 8:
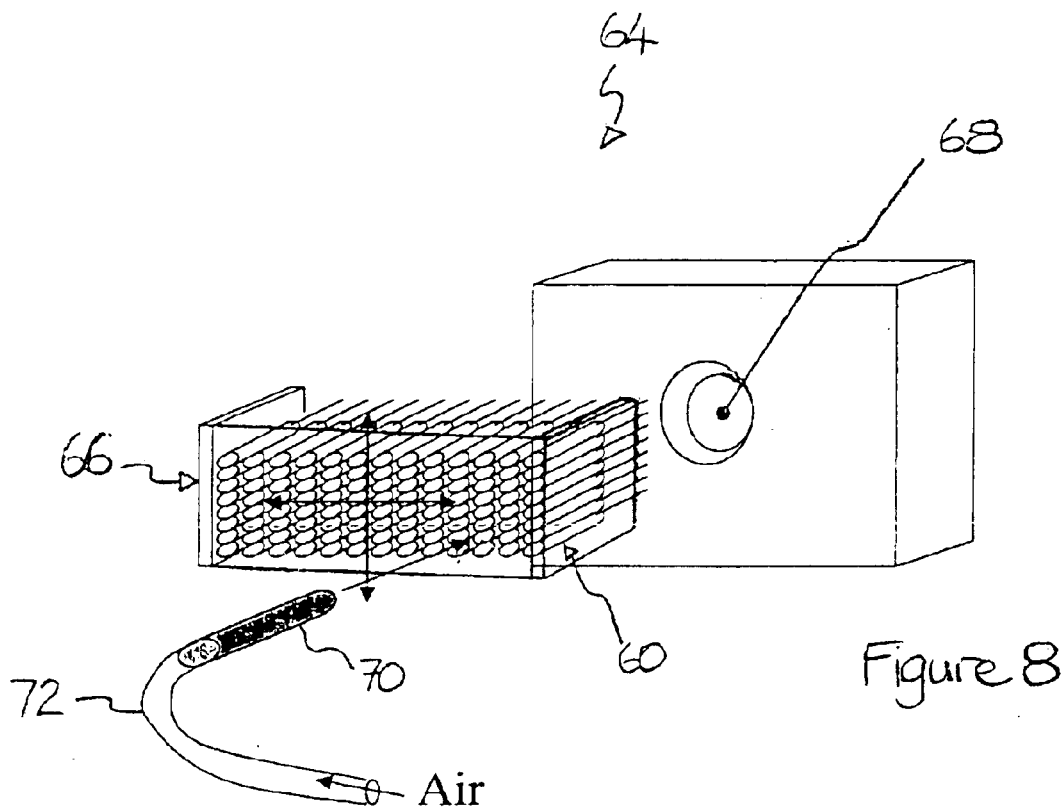
FIG. 8 depicts a nano-needle array apparatus placed into a mass spectrometer apparatus suitable for practicing the method of the invention.
Figure 9:
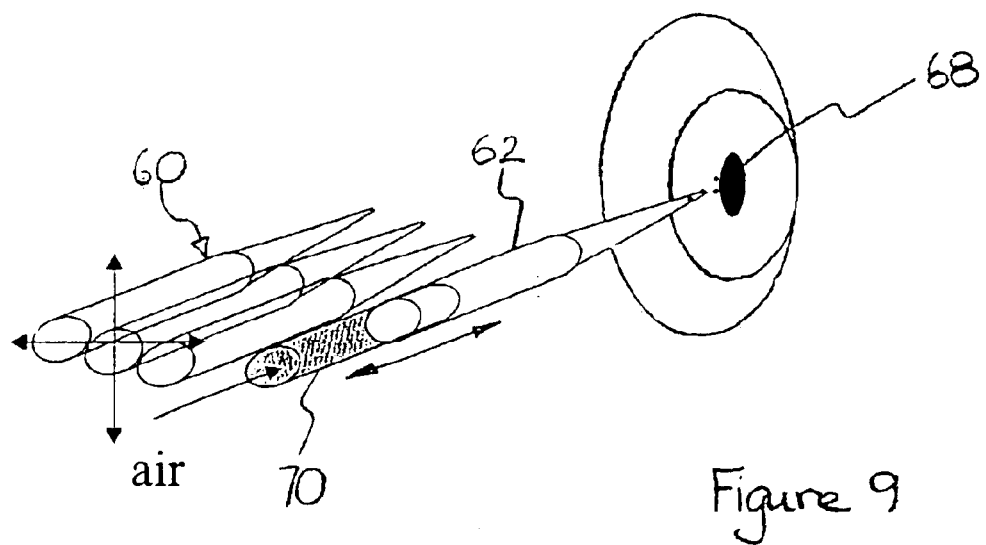
FIG. 9 is a detailed schematic representation of a nano-needle apparatus aligned with a mass spectrometer inlet orifice, which would be suitable for conducting the method of the invention.

Following collection of digested eluate in nano-needle array 60, nano-needle array 60 is disengaged from collection array 36 and placed into manifold 66, as depicted in apparatus 64 of FIG. 8. Manifold 66 positions nano-needle array 60 in front of mass spectrometer orifice 68. In a preferred embodiment, the mass spectrometer is suitable for electrospray ionization (ESI). In an alternative embodiment, the mass spectrometer is suitable for matrix assisted laser desorbtion ionization (MALDI) mass spectrometry. Precise alignment of each nano-needle 62 with mass spectrometer orifice 68 can be achieved by two-dimensional movement of manifold 66. Hollow push rod 70 engages at the back of nano-needle 62, and mechanically pushes the needle tip of nano-needle 62 to mass spectrometer orifice 68. Application of air pressure by means of directing air flow through flexible pipe 72 causes the spraying of digested eluate from nano-needle 62 into mass spectrometer orifice 68, thereby mediating mass spectrometry fingerprint analysis of digested eluate. After mass spectrometry analysis, push rod 70 is retracted and engaged with the next aligned nano-needle 62. In a preferred embodiment, coordinated movement of push rod 70 and mass spectrometer data acquisition is computer-controlled. A detailed schematic of nano-needle 62 alignment with mass spectrometer orifice 68 and engagement of push rod 70 is provided in FIG. 9.

Equivalents

While this invention has been particularly shown and described with references to preferred embodiments thereof, it will be understood by those skilled in the art that various changes in form and details may be made therein without departing from the scope of the invention encompassed by the appended claims.

What is claimed is:

1. An apparatus for screening a proteome, comprising:
   a) an array of affinity elements, said affinity elements including at least one ligand and said at least one ligand being bound to a compound of the proteome;
   b) a means for applying a centrifugal force to the array whereby a flow of eluent can be directed through the array by centrifugal force and can release the compound of the proteome that is bound to the at least one ligand, thereby eluting the compound of the proteome from the array as a component of an eluate for screening of the proteome;
   c) at least one swing basket supporting the array, said swing basket including a hinge, whereby rotation of the swing basket about an axis causes the swing basket to rotate about the hinge, thereby causing the centrifugal force on the array to be parallel to the flow of eluent through the affinity elements of the array;
   d) at least one tube sheet having a plurality of tube elements positioned between the hinge and the array, the plurality of tube elements aligned with the affinity elements of the array, the tube sheet being moveable laterally relative to the flow of eluent from the tube sheet through the affinity elements of the array;
   e) a plurality of orifices, defined by the tube sheet and heated between at least a portion of the tube elements of the tube sheet; and
   f) a moveable set of collection tubes aligned with the affinity elements of the array, the set of collection tubes being positioned on a side of the array opposite to that of the tube sheet to contain the eluate.

2. The apparatus of claim 1, wherein the tube sheet is moveable between at least three positions, wherein each affinity element of the array is aligned with two different tubes of the tube sheet in two of the positions, and aligned with one of the orifices in the third position.

3. The apparatus of claim 2, further including a centrifuge basket within which the swing basket is supported.

4. The apparatus of claim 3, further including means for continuously directing at least one wash solution through the array.

5. The apparatus of claim 4, further including a wash solution source, and wherein the array is in fluid communication with the wash solution source when the orifices of the tube sheet are aligned with affinity elements of the array.

6. The apparatus of claim 3, wherein movement of the tube sheet relative to the array causes the affinity elements of the array to be aligned and in fluid communication with either the tube elements of the tube sheet containing components of a proteome, orifices of the tube sheet whereby fluid communication is established with a wash source, or the tube elements of the tube sheet containing components of a chemical library.

7. The apparatus of claim 6, further including magnetic means for moving the tube sheet.

8. The apparatus of claim 7, wherein the collection tubes are moveable between a position that causes eluate from the array of affinity elements to be collected in the centrifuge basket and a position that causes eluate from the array of affinity elements to be collected in the collection tubes.

9. The apparatus of claim 8, wherein the collection tubes are aligned for collection of eluate when the tube sheet is aligned for delivery of components of a chemical library to the affinity elements of the array.

10. The apparatus of claim 9, wherein the elements of the tube sheet each include a disc that indicates the level of fluid in each element.

11. The apparatus of claim 1 further including a nano-needle array, wherein the nano-needle array is aligned with the array of affinity elements when the movable set of collection tubes is moved out of alignment with the affinity elements, such that the nano-needle array collects the eluate.

12. The apparatus of claim 11, wherein a nano-needle of the nano-needle array further includes an amount of hydrophobic resin in a range of between about 2 ml and about 4 ml.

13. The apparatus of claim 12, wherein the nano-needle array can be detached from the array of affinity elements and mounted in a mass spectrometer, such that a nano-needle of the nano-needle array is aligned with an inlet orifice of the mass spectrometer for delivery of eluate to be analyzed by mass spectrometry.

14. The apparatus of claim 13, wherein the mass spectrometry is nano spray mass spectrometry.

15. The apparatus of claim 14, wherein the nano-spray mass spectrometry is electrospray ionization.

16. The apparatus of claim 15, wherein the delivery of the eluate to be analyzed by mass spectrometry is mediated by air pressure directed through a hollow push rod that is attached to the nano-needle that contains the eluate, thereby producing a spray of eluate directed into the inlet orifice of the mass spectrometer, thus delivering the eluate into the mass spectrometer for analysis.

17. The apparatus of claim 16, wherein the nano-needle array can be moved in at least two dimensions to align a nano-needle of the nano-needle array with the inlet orifice of the mass spectrometer for delivery of the eluate to be analyzed by mass spectrometry.

18. The apparatus of claim 17, wherein the alignment of a nano-needle of the nano-needle array is controlled by a computer.

* * * * *

UNITED STATES PATENT AND TRADEMARK OFFICE
CERTIFICATE OF CORRECTION

| | | |
|---|---|---|
| PATENT NO. | : 6,716,395 B2 | Page 1 of 1 |
| APPLICATION NO. | : 10/022931 | |
| DATED | : April 6, 2004 | |
| INVENTOR(S) | : Haystead et al. | |

It is certified that error appears in the above-identified patent and that said Letters Patent is hereby corrected as shown below:

<u>Column 7</u>,

Line 57, in claim 1, "heated" should read --located--.

Signed and Sealed this

Twenty-ninth Day of January, 2008

JON W. DUDAS
*Director of the United States Patent and Trademark Office*